United States Patent [19]

Clarke et al.

[11] Patent Number: 5,133,979
[45] Date of Patent: Jul. 28, 1992

[54] PLANT GUM MATERIAL AND USE THEREOF IN FOOD PRODUCTS

[75] Inventors: Adrienne E. Clarke, Parkville; Antony Bacic, Eltham; Alan G. Lane, Ashfield, all of Australia

[73] Assignees: Bio Polymers Pty. Ltd., Victoria; Commonwealth Scientific and Industrial Research Organisation, Campbell, both of Australia

[21] Appl. No.: 415,263

[22] PCT Filed: Feb. 26, 1988

[86] PCT No.: PCT/AU88/00052
§ 371 Date: Oct. 25, 1989
§ 102(e) Date: Oct. 25, 1989

[87] PCT Pub. No.: WO88/06627
PCT Pub. Date: Sep. 7, 1988

[30] Foreign Application Priority Data

Feb. 26, 1987 [AU] Australia ............................ 0556/87
Sep. 22, 1987 [AU] Australia ............................ 4502/87

[51] Int. Cl.$^5$ ........................................... A23L 1/0532
[52] U.S. Cl. ...................................... 426/49; 426/573; 426/577; 435/240.4; 435/240.46; 536/2; 536/3; 536/52; 536/114
[58] Field of Search ........................ 435/240.4, 240.46; 536/52, 114, 2, 3; 426/655, 605, 577, 573, 601, 49

[56] References Cited

U.S. PATENT DOCUMENTS

| | | | |
|---|---|---|---|
| 2,747,334 | 5/1956 | Routien | 435/240.46 |
| 3,184,887 | 5/1965 | Winter | 435/240.46 |
| 3,955,317 | 5/1976 | Gudin | 435/240.46 |
| 4,241,186 | 12/1980 | Roth | 536/2 |
| 4,568,739 | 2/1986 | Jaskowski | 536/2 |
| 4,686,187 | 8/1987 | Sakai | 426/49 |
| 4,703,117 | 10/1987 | Fischer | 536/114 |
| 4,784,957 | 11/1988 | Medgyesy | 435/240.4 |
| 4,835,262 | 5/1989 | Sakai | 536/2 |

FOREIGN PATENT DOCUMENTS

| | | | |
|---|---|---|---|
| 62457 | 1/1982 | European Pat. Off. | |
| 0050562 | 4/1982 | European Pat. Off. | 435/240.46 |
| 52001 | 5/1982 | European Pat. Off. | |
| 0121981 | 10/1984 | European Pat. Off. | 435/240.40 |
| 0062457 | 10/1986 | European Pat. Off. | |
| 225496 | 11/1986 | European Pat. Off. | |
| 285829 | 7/1988 | European Pat. Off. | |
| 0154575 | 4/1982 | Fed. Rep. of Germany | 426/605 |
| 56-164148 | 10/1981 | Japan | |
| 56-164149 | 10/1981 | Japan | |
| 57-206360 | 12/1982 | Japan | 426/605 |
| 60-49604 | 3/1985 | Japan | |
| 60-172927 | 9/1985 | Japan | |
| 1209599 | 9/1986 | Japan | |

OTHER PUBLICATIONS

Bacic et al. (1987) Aust. J. Plant Physiol. 14:633–641.
Barnoud et al. (1977) Physiologie Vegetale 15:153–161.
Wallner et al. (1986) J. Amer. Soc. Horticultural Sci. 111(5):769–773.
Conrad et al. (1982) Protoplasma 111:196–204.
Olson et al. (1969) Plant Physiol. 44:1594–1600.
Takeuchi et al. (1978) Physiol Plant 42:21–28 (Abstract).
Takeuchi et al. (1978) Chemical Abstracts 88:101687z.
Meer et al. (1975) Food Technology 29:22–30.
Chambat et al. (1987) Food Hydrocolloids 1(516):555–556.
Fincher et al. (1983) Ann. Rev. Plant Physiol. 34:47–70.
Clarke, A. E., et al. (1979) Phytochemistry 18:521–540.
Sandford, P. A. and Baird, J. (1983) in The Polysaccharides, vol. 2, Aspinal, G. O. (ed) Academic Press, N.Y.

Primary Examiner—Carolyn Paden
Attorney, Agent, or Firm—Greenlee & Winner

[57] ABSTRACT

A method for the production of a plant gum product which comprises the steps of culturing gum-secreting plant cells in tissue culture in the presence of a culture medium; and recovering the gum product secreted by the cells from the culture medium. The gum product may be used in a food product, for example, as an emulsifying or stabilizing agent.

10 Claims, 1 Drawing Sheet

PLANT GUM MATERIAL AND USE THEREOF IN FOOD PRODUCTS

FIELD OF THE INVENTION

This invention relates to the use of a plant gum material, produced from plant cells in tissue culture, as an additive to formulations in the food industry. In particular, the present invention relates to the use of this plant gum product as a substitute for gums such as gum arabic (a widely-used emulsion stabilizer) and guar gum (a widely-used thickener) in the food industry, and examples are provided herein of the use of this plant gum product as an emulsion stabilizer, emulsifier, thickening agent and texture modifier, however the invention is not limited to these uses.

BACKGROUND OF THE INVENTION

Complex carbohydrates and polysaccharides have numerous functions in food products such as emulsifiers, emulsion stabilizers, thickening and gelling agents and suspending agents (Sandford and Baird, 1983). Most polysaccharides function by altering the properties of aqueous solutions or dispersions primarily via their ability to bind water molecules and ions; they also interact with each other through "junction zone" formation (Rees, 1972).

Several plant families include species that exude gums, and those that produce copious quantities represent a ready supply of gums. In addition to exudate gums, gums are also obtained from seeds, for example guar gum and from algae, e.g. agar. More recently, gums have been produced by microbial fermentation under controlled conditions, and xanthan gum which is produced in this manner has recently achieved commercial significance. In general, these gums or mucilages are carbohydrate-enriched polymers of high molecular weight composed of acidic and/or neutral monosaccharide building units joined by glycosidic bonds.

Gum arabic is the dried exudate from species of the acacia tree (*Acacia senegal*) found in various tropical and semitropical areas of the world. The acacia trees produce large quantities of gum arabic under adverse conditions, lack of moisture, poor nutrition and high temperatures. The gum is collected as a natural exudate from the surface of wounds generally produced deliberately in cultivated trees. The exudate is dried to form a product which is completely soluble in hot or cold water, yielding a viscous solution of mucilage finding wide use as a thickening agent and emulsion stabilizer in a wide range of foods, beverages and confectionery and also in adhesives, inks, textiles, printing and cosmetics.

SUMMARY OF THE INVENTION

Suspension-cultured plant cells secrete a mixture of complex carbohydrates and glycoproteins into the culture medium. The major classes of complex carbohydrate polymers are proteoglycans (e.g. arabinogalactan-proteins (AGPs)), polysaccharides (e.g. neutral and acidic pectins), hetero- and homo-glucans, heteroxylans, and hetero- and homo-mannans (McNeil et al., 1984). It has now been found that a mixture of these polymers produced by cells derived from tissues of plants in a variety of plant families is a useful substitute for plant gums in the food industry, and may be used, for example, as a substitute for gum arabic as an emulsifying, stabilising and/or thickening agent.

Plants of many plant families can be taken into callus (solid) culture and then into liquid suspension culture. It is known that AGPs and other complex carbohydrates and proteins are secreted by many such cell lines (Clarke, et al., 1979; Fincher, et al., 1983). In accordance with the present invention, the cells of any of the complex carbohydrate-secreting plants are cultured in tissue culture in an appropriate growth medium so that a mixture of complex carbohydrates and (glyco)-proteins is secreted into the culture medium. In one particular aspect of the present invention, it has been found that tissue cultures derived from the pear, Pyrus, sweet cherry, *Prunus avium*, and the rose, Rosa, secrete high yields of complex carbohydrates. This may be related to a capacity of the trees themselves to produce gums as a wound response.

According to one aspect of the present invention, there is provided a method for the production of a plant gum product, which comprises the steps of:
  (a) culturing gum-secreting plant cells in tissue culture in the presence of a culture medium; and
  (b) recovering the gum product secreted by the cells from the culture medium.

The present invention also extends to the plant gum product which can be produced by this method.

According to another aspect, the present invention provides a food product, characterised in that it contains a plant gum product secreted by suspension-cultured plant cells. This product may be either a human or animal food product.

The present invention also extends to a method of preparing a food product which is characterised by the use of a plant gum product as outlined above.

In one particular embodiment of the present invention, the food product may comprise a stable emulsion characterised in that it includes a plant gum product as described above as an emulsifying or stabilizing agent. Such a stable emulsion may be used, for example, as a base for a mayonnaise. As is well known in the food industry, a variety of mayonnaises for different purposes (sea foods, egg dishes, green salads, potato salads, etc) can be prepared using various combinations of colourings and flavourings, which are added to the oil-water mixture before or after emulsifying.

In other embodiments of the invention, the plant gum product may be added to the food product as a thickening or gelling agent, a texture modifier, a binding or coating agent, or the like.

DETAILED DESCRIPTION OF THE INVENTION

Figure 1:
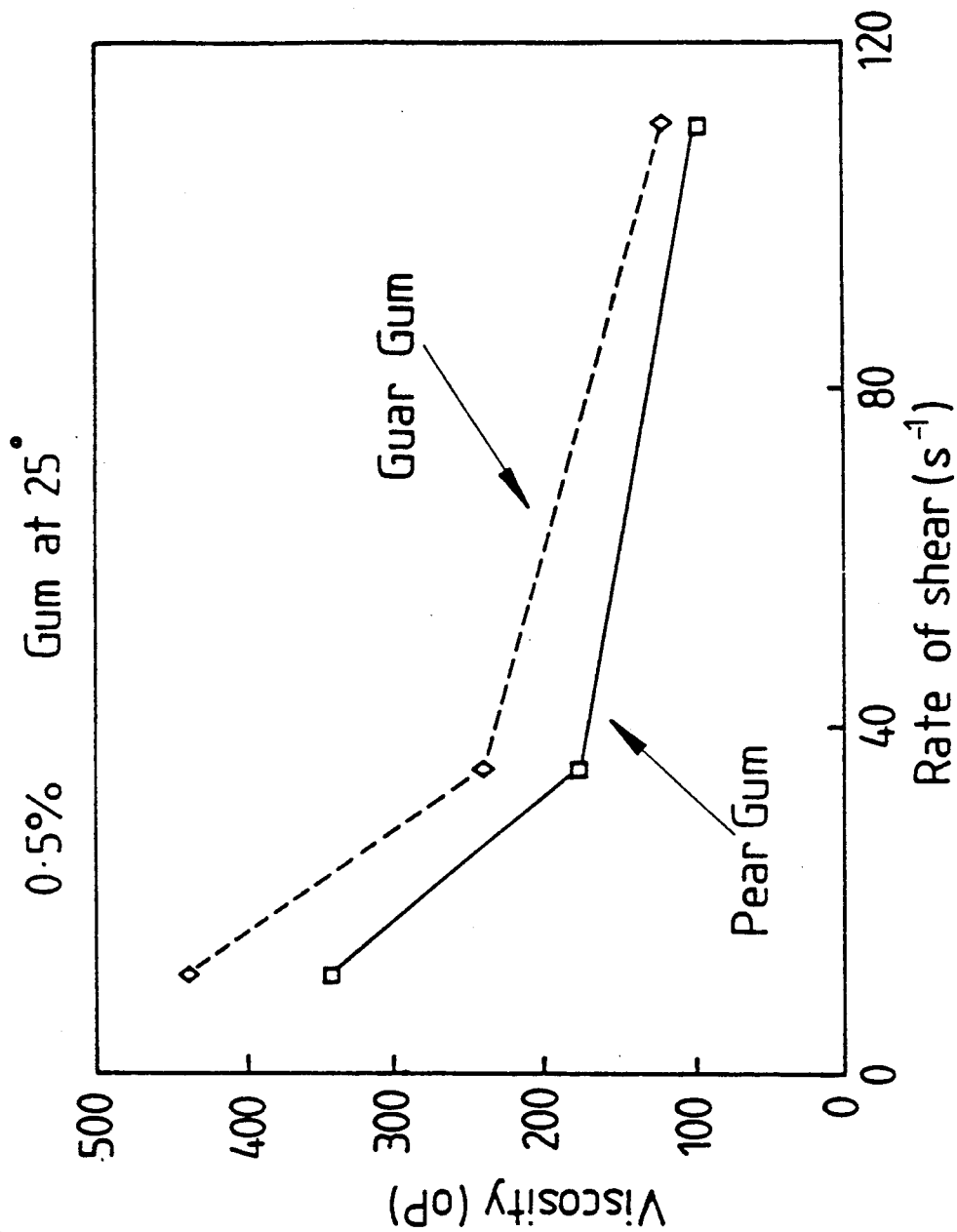
FIG. 1 is a graph of the viscosities of 0.5% (w/v) aqueous mixture of the subject gum product and of guar gum as a function of sheer rate.

As broadly outlined above, the plant gum product which is used as in accordance with the present invention is a product which is secreted by suspension-cultured plant cells. The cells of a gum-secreting plant, which may for example be initiated from a leaf, style, anther or stem of the plant, are taken into suspension culture and the gums secreted into the culture mixture are recovered to produce a gum product. The recovery may be by any suitable method such as selective filtration and/or alcohol precipitation.

By way of example of the present invention, the gum product may comprise a material secreted by suspension-cultured cells of the pear (Pyrus). Such cells have been found to secrete a mixture of complex carbohydrates at yields of 5.26 mg carbohydrate/ml of culture fluid as determined by the method of Dubois et al. (1956). The mixture contains 82% neutral monosaccharides and 14% acidic ("pectins") monosaccharides. Acidic residues were determined by the method of Blumenkrantz and Asboe-Hansen (1973). It also contains approximately 4% protein, as determined by the Bradford (1976) procedure. In this example, the arabinogalactan-protein (AGP) content of the gum product was 8.9% (w/w) of the total carbohydrate as determined by the single-radial diffusion assay of van Holst and Clarke (1985). The neutral monosaccharide composition of one example of this mixture, determined as described in Bacic et al. (1986), is as follows:

| Monosaccharide | % w/w |
| --- | --- |
| Rhamnose | 2 |
| Fucose | 3 |
| Arabinose | 16 |
| Xylose | 11 |
| Mannose | 4 |
| Galactose | 18 |
| Glucose | 46 |

In other examples, the same major monosaccharides are present, but the proportions of these and the macromolecules, such as polysaccharides and (glyco)proteins may vary. Arabinose, xylose, galactose and glucose are the major neutral monosaccharides whereas rhamnose, fucose and mannose are characteristically minor neutral monosaccharides.

There is no single measurement or parameter which indicates suitability of a gum product for use in foods. Instead, a number of physical measurements are made (e.g. viscosity, shear rate, gel strength, melting temperature) which, when combined with subjective assessments of palatability (e.g. flavour "body", "mouth feel", stickiness) give an indication as to the likely food uses for the gum product. The following general examples of the use of the gum product prepared from suspension-cultured cells of Pyrus as described above, and compared with gum arabic (a widely-used emulsion stabilizer) and guar gum (a widely-used thickener), are included to illustrate some of the food uses of the product, as follows:

1. Thickening Agent

The gum product exhibits appropriate viscosity and shear thinning properties to make it suitable for use as a thickening agent in food products. The measured viscosity of the gum product was comparable with that of guar gum at the same concentration (0.5% w/v).

Reduced viscosity of the gum product with increasing shear was similar to that seen with guar gum. That is to say, the gum product demonstrated thixotropic properties similar to guar.

The effect of shear rate on measured viscosity of the gum product and guar gum is shown in FIG. 1.

2. Emulsion Stabilizer/Emulsifier

The gum product at 0.28% (w/v) possessed excellent emulsion stabilizing properties: approximately three times the concentration of gum arabic (1.0% (w/v)) was needed to produce an equivalent emulsion which could be handled without disintegrating and was similar to tofu, bean curd or baked custard in texture and physical strength. However, the gum arabic emulsion obtained at this relatively high concentration (1.0% (w/v)) was not so stable upon storage as that produced by the gum product at the much lower concentration (0.28% (w/v)). In a comparative trial, oil was coloured by the addition of an oil-soluble dye, Sudan Black, to allow the effect to be photographed. The results clearly show the oil in the gum arabic emulsion separating and rising to the surface after storage, whereas the emulsion produced by the gum product remains stable, with the oil uniformly distributed throughout.

3. Texture Modifier

The gum product has a good "mouth feel" and almost no flavour, making it well-suited to incorporation in prepared food formulation. The gel is soft yet coherent and "clean" on the tongue, similar in the mouth to firm yoghurt or a gel of pectin or gelatin. By contrast, a solution of guar at the same concentration had a slimy mouth feel and a strong "beany" flavour.

These general examples of the use of the gum product in food products in accordance with the present invention indicate the potential of gums and emulsion stabilizers produced by plant cell culture for the food industry.

It will, of course, be appreciated that the in vitro production of a plant gum product in accordance with the present invention may offer significant commercial advantages in terms of production costs and yields when compared with the previously known processes for the production of gums such as gum arabic which rely on hand collection of natural gum exudates over a period of many weeks. Furthermore, since the supply of these gums from the traditional sources has not always been able to keep up with the demands of industry, particularly the food industry, there is a need for a more efficient and economical source of a suitable gum product of the type provided by the present invention.

The following examples illustrate, by way of example only, the production and use of a gum product in accordance with the present invention as an emulsion stabilizer in the production of a mayonnaise. It will, of course, be appreciated that the product of this invention is equally applicable for use as an emulsifying agent or stabilizer in many other emulsion products in the food industry.

EXAMPLE 1 a. Production and Recovery of Gum Product

The gum product secreted from suspension-cultured cells of Pyrus was produced and recovered in the following manner:

Cultivation of cells

Medium (700 ml) in wide-mouth Erlenmyer flasks (2 liters capacity) was sterilized by autoclaving (110° C., 20 minutes) and inoculated with approximately 10% (v/v) of a 7 day-old culture of suspension-cultured cells of Pyrus initiated from callus (solid) culture and growing in the same medium. Flasks were incubated on a rotary shaketable (100 rpm) at 27° C. for 14 days. The composition of the culture medium was as follows, made up to 1 liter with Millipore filtered water:

| Macro elements | 100 ml |
| --- | --- |
| Micro elements | 1 ml |
| Vitamins | 1 ml |
| CaCl$_2$ | 2.5 ml |
| Fe.EDTA | 2.5 ml |
| Asparagine | 180 mg |
| Ascorbate | 50 mg |
| Thiourea | 25 mg |
| Sucrose | 40 g |

-continued

| KI | 0.5 ml |
| --- | --- |
| 2,4-D (2,4-dichlorophenoxy acetic acid)* | 1 ml |
| Adjust pH to 5.8–6.0 with KOH. | |

*(50 mg in 2-3 ml EtOH, warmed gently to dissolve and injected into 50 ml flask containing filtered water.)

Harvesting and work-up of plant gum product

The culture (2.8 liters) was filtered through a double layer of gauze to remove the cells. The filtrate (fluid) (1.4 liters), containing 5.26 mg of complex carbohydrate/ml was placed in a dialysis sack (approx. 10 cm diameter) and concentrated to approximately half volume using "Carbowax" (polyethylene glycol) at 1° C. for approximately 24h. The concentrated product was then dialysed for 24h against approx. 40 liters of distilled water containing 0.1% (w/v) sodium azide as an antimicrobial agent, followed by 24h against the same volume of distilled water in which the sodium azide had been omitted. The dialysis was performed under constant mixing conditions by bubbling the water with air from a small air pump. The final volume of the plant gum product was 570 ml. The carbohydrate content of the product was 13 mg/ml.

b. Preparation of Food Product

A stable oil-in-water emulsion was prepared, with the gum product secreted from plant cell suspension cultures of Pyrus as emulsifying agent, and used as the base for making a variety of mayonnaises.

Vegetable oil (e.g. Meadowlea blended vegetable oil; 20 ml) was emulsified with 80 ml of aqueous phase containing 0.25-0.5 g of gum product and sufficient acetic acid to provide the desired flavour. Typically, this is obtained by adding 1-3 ml of glacial acetic acid or 10-30 ml of cider vinegar or tarragon vinegar.

The two liquids were emulsified with an emulsifying machine such as an "Ultra-Turrax" (Janke & Kunkel KG), typically on a power setting of 90 volts for 30 seconds, followed by 30 seconds at a setting of 140 volts.

As described above, various combinations of colourings and flavourings may be added to the oil-water mixture before or after emulsifying in order to produce a variety of mayonnaises for different purposes. Examples of colourings and flavourings which have been used in various combinations include tarragon, salt, garlic powder, onion powder, basil, mustard, tahini, MSG, black pepper, paprika and beta-carotene.

EXAMPLE 2

The production of gum product secreted from suspension-cultured cells of Pyrus as described in Example 1(a), has been scaled up to a 20 liter glass bottle containing 15 liters of the culture medium as previously described. The medium was inoculated with 2 liters of log phase pear cell suspension-culture and aerated with a sparging device which creates a dispersion of fine bubbles at the bottom of the bottle (air flow 10 l air/min). Following incubation at 27° C. for 14 days, the gum product was harvested and worked-up as described in Example 1(a) to produce a product with similar characteristics to the product of Example 1.

Those skilled in the art will appreciate that the invention described herein is susceptible to variations and modifications other than those specifically described. It is to be understood that the invention includes all such variations and modifications which fall within its spirit and scope.

We claim:

1. A plant gum product comprising glycoprotein and complex carbohydrate, produced by a method which comprises the steps of:
    (a) culturing gum-secreting plant cells derived from tissues of vascular plants in suspension culture in the presence of a culture medium; and
    (b) recovering the gum product secreted by the cells from the culture medium,
wherein the plant cells are derived from the pear, Pyrus, sweet cherry, Prunus avium, or the rose, Rosa.

2. A food product, characterised in that it contains a plant gum product secreted by suspension-cultured gum-secreting plant cells derived from tissues of vascular plants.

3. A food product according to claim 2, characterized in that it contains a plant gum product comprising glycoprotein and complex carbohydrate, produced by a method which comrpises the steps of:
    (a) culturing gum-secreting plant cells derived from tissues of vascular plants in suspension culture in the presence of a culture medium,
    (b) recovering the gum product secreted by the cells from the culture medium, wherein the pant cells are derived from the pear, Pyrus, sweet cherry, Prunus avium, or the rose, Rosa.

4. A food product according to claim 2, comprising a stable emulsion including said plant gum product as an emulsifying or stabilizing agent.

5. A food product according to claim 4, wherein said emulsion is an oil-in-water emulsion.

6. A food product according to claim 4, wherein said stable emulsion comprises a mayonnaise base.

7. A food product according to claim 3, wherein said plant gum is that of pear, Pyrus cells.

8. A food product according to claim 3, wherein said plant gum is added to said food product at 0.25 to 0.5% (w/v).

9. A food product according to claim 8, wherein said plant gum is added to said food product at 0.28% (w/v).

10. A food product according to claim 2, comprising said plant gum product as a thickening or gelling agent, a texture modifier, or a binding or coating agent.

* * * * *